US00RE47921E

(19) United States
(12) Reissued Patent
Patwardhan

(10) Patent Number: US RE47,921 E
(45) Date of Reissued Patent: Mar. 31, 2020

(54) REFLECTANCE IMAGING AND ANALYSIS FOR EVALUATING TISSUE PIGMENTATION

(71) Applicant: Canfield Scientific, Incorporated, Fairfield, NJ (US)

(72) Inventor: Sachin V. Patwardhan, Morris Plains, NJ (US)

(73) Assignee: Canfield Scientific, Incorporated, Parsippany, NJ (US)

(21) Appl. No.: 14/813,082

(22) Filed: Jul. 29, 2015

Related U.S. Patent Documents

Reissue of:

(64) Patent No.: 8,498,460
Issued: Jul. 30, 2013
Appl. No.: 13/032,341
Filed: Feb. 22, 2011

U.S. Applications:

(60) Provisional application No. 61/306,698, filed on Feb. 22, 2010.

(51) Int. Cl.

*G06K 9/00* (2006.01)
*G06T 7/00* (2017.01)
*A61B 5/00* (2006.01)

(52) U.S. Cl.

CPC ..... *G06T 7/0012* (2013.01); *A61B 5/0077* (2013.01); *A61B 5/441* (2013.01);

(Continued)

(58) Field of Classification Search

CPC ..... A61B 5/0077; A61B 5/441; G06T 2207/10024; G06T 2207/30088; G06T 7/0012

(Continued)

(56) References Cited

U.S. PATENT DOCUMENTS 5,016,173 A * 5/1991 Kenet ..... A61B 5/0059 382/128
5,241,468 A * 8/1993 Kenet ..... A61B 5/0059 382/128

(Continued)

OTHER PUBLICATIONS

Shinji Umeyama , Guy Godin, Separation of Diffuse and Specular Components of Surface Reflection by Use of Polarization and Statistical Analysis of Images, IEEE Transactions on Pattern Analysis and Machine Intelligence, v.26 n.5, p. 639-647, May 2004.*

(Continued)

*Primary Examiner* — Colin M LaRose
(74) *Attorney, Agent, or Firm* — Brosemer Kolefas & Assoc., LLC

(57) ABSTRACT

Methods and apparatus are described that provide the ability to estimate the diffuse reflection component of an image of tissue such as skin captured without cross-polarization. It is thereby possible to estimate skin pigmentation information from an image of skin captured conventionally, such as, for example, a total reflection image, obtained in a conventional manner by shining white light on the skin and capturing the reflected light. The image may also be a partially diffuse reflection image, such as a low quality cross-polarized image. The diffuse reflection component of a captured image can then be further processed to obtain Red and Brown pigmentation images, useful for indicating the distribution of hemoglobin and melanin, the primary chromophores of skin. Additionally, a standard captured image of skin can be analyzed to obtain an estimate of the surface reflection (Continued)

component of the reflected light. The surface reflection component can then be used to generate a surface reflection image, useful for showing the distribution of light on the skin and to highlight superficial features such as wrinkles, fine lines, folds, pores, texture, and visible spots.

42 Claims, 4 Drawing Sheets

(52) U.S. Cl.
CPC ..... *G06T 2207/10024* (2013.01); *G06T 2207/30088* (2013.01)

(58) Field of Classification Search
USPC ..... 382/128, 274
See application file for complete search history.

(56) References Cited

U.S. PATENT DOCUMENTS 6,081,612 A * 6/2000 Gutkowicz-Krusin ..... A61B 5/0071 382/128
7,233,693 B2 * 6/2007 Momma ..... A61B 5/0064 382/162
7,689,035 B2 * 3/2010 Mallick ..... G06T 5/30 382/163
8,154,612 B2 * 4/2012 Quan ..... G06K 9/4652 348/222.1
2004/0267102 A1 * 12/2004 Skladnev ..... A61B 5/442 600/315
2007/0132759 A1 * 6/2007 Mallick et al. ..... 345/426
2007/0229658 A1 * 10/2007 Kanamori et al. ..... 348/135
2008/0186390 A1 * 8/2008 Sato ..... G06T 3/4053 348/222.1

OTHER PUBLICATIONS

Jae Byung Park, "Detection of Specular Highlights in Color Images using a New Color Space Transformation," 2004 IEEE International Conference on Robotics and Biomimetics, Shenyang, 2004, pp. 737-741.*
N. Ojima et al., "Quantification method for the appearance of melanin pigmentation using independent component analysis", SPIE, Jan. 2005, pp. 22-32.
N. Tsumura et al, "Independent-component analysis of skin color image", Journal of the Optical Soc. of Amer., vol. 16, No. 9, Sep. 1, 1999, p. 2169.
Y. Moriuchi et al, "Precise Analysis of Spectral Reflectance Properties of Cosmetic Foundation", Image Analysis, Springer, Jun. 15, 2009, pp. 138-148.
Y. Mukaigawa et al, "Analysis of subsurface scattering under generic illumination", 19th Int'l Conf. on Pattern Recognition, Dec. 8, 2008, pp. 1-5.
R. Demirli et al, "RBX(TM) Technology Overview", Canfield Scientific, 2007.
International Search Report and Written Opinion for counterpart application PCT/US2011/025731.

* cited by examiner

REFLECTANCE IMAGING AND ANALYSIS FOR EVALUATING TISSUE PIGMENTATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED PATENT APPLICATIONS

The present application claims priority from U.S. Provisional Patent Application No. 61/306,698, filed on Feb. 22, 2010, which is incorporated herein by reference in its entirety.

FIELD OF THE INVENTION

The present invention relates to computer-aided skin analysis, and more particularly to reflectance imaging and analysis for evaluating reflection components and skin tissue pigmentation.

BACKGROUND INFORMATION

Spectrometry is a proven technique for measuring the concentration of skin constituents like melanin and hemoglobin through the spectrum emitted or absorbed by them. It has been used to study the interaction between radiation and matter as a function of wavelength or frequency. A drawback of this technique is that the measurements are typically done on a very small tissue area using a point source-detector pair. For a larger field of view or area-of-interest, either multi-spectral imaging or time/frequency resolved measurements have been used. In typical implementations of these techniques, measurements are evaluated against an assumed light-tissue interaction model and the unknown optical properties of the underlying tissue are solved as an inversion problem. While the aforementioned techniques can provide true quantitative, and in some cases even depth-dependent (i.e., three-dimensional) information, the instrumentation and processing required are complex.

Conventional reflectance imaging of skin typically entails illuminating the skin with white light and capturing the light reflected therefrom. (A conventional reflectance image may also be referred to as a standard captured image, or a total reflection image among other commonly used terms.) The reflected light has two components: a specular or surface reflection component, and a diffuse reflection component. When separated from each other, each component provides useful information about the imaged tissue. The surface reflection component is useful for analyzing topological characteristics of tissue such as surface texture and visible features such as wrinkles and pores. The diffuse reflection component, which is due to light that has interacted with the tissue interior, conveys information about the optical properties of the tissue such as the distribution of chromophores like melanin and hemoglobin. Some photons of the incident light penetrate within the tissue and undergo multiple scattering and absorption events before some of those photons are backscattered as diffuse reflected light. The average penetration depth of a photon is dependent on its wavelength, with longer-wavelength photons penetrating deeper into the tissue. The wavelength- (or color-) dependent average penetration depth of photons is illustrated in FIG. 1.

Cross-polarized and parallel-polarized imaging have been the preferred techniques used for respectively capturing diffuse and surface reflection components independently. In a typical implementation illustrated in FIG. 1, a broad-band light source 10 illuminates a skin sample while images are captured using a digital color camera 20 with polarizing filters 15, 25 in both the illumination and reflection paths. For capturing diffuse reflection images, the polarization axes of filters 15, 25 are oriented perpendicular to each other. A part 51 of the polarized incident light 50 is reflected back from the skin surface. This surface reflection component 51 maintains the same polarization as that of the incident light 50 and is blocked by the detector side polarizing filter 25 due to its orthogonal orientation relative to filter 15 in the illumination path. Another part 52 of the polarized incident light 50 penetrates the skin surface and undergoes multiple scattering and absorption events before some of those photons are backscattered as diffuse reflected light 53. Due to scattering, the diffuse reflected light 53 has lost all its polarization and hence a portion thereof is able to pass through the detector side polarizing filter 25. For capturing surface reflection images, the polarization axes of the filters 15, 25 are oriented parallel to each other.

In addition to cross-polarized imaging as described above, diffuse reflection images can also be captured using a dark field illumination technique where the light is incident at an angle only on the edge of the skin area being imaged while the detector is allowed to only capture reflected light which is almost perpendicular to the skin surface. Although dark-field illumination techniques do not require polarizing filters, they have several drawbacks. The angle of illumination is dependent on the area being illuminated. If the angle of incidence is too shallow or too direct, then there will be a dark spot in the center where no light has reached. The area that can be imaged is very small since it will have a radius equal to the average of the total scattering length of the light in tissue. Some form of a ring light source of appropriate diameter is thus required.

Diffuse reflection images, obtained using either cross-polarized imaging or dark-field illumination techniques, have been analyzed for the purpose of evaluating tissue pigmentation and distribution information. Evaluation of diffuse reflection color images for tissue pigmentation information has been carried out using various tools such as: 1) color-space transformations; 2) various combinations of color-spaces; 3) optical models of light-tissue interaction, treating the three color channels of the images as multi-spectral measurements; and 4) principle component analysis (PCA) or independent component analysis (ICA) techniques with or without a linear or non-linear tissue absorption models.

Another technique for evaluating tissue pigmentation, developed by Canfield Imaging Systems, is the RBX technique which can transform Red/Green/Blue (RGB) cross-polarized skin images into Red and Brown representations indicative of hemoglobin and melanin distributions, respectively. (See R. Demirli et al., "RBX Technology Overview", Canfield Imaging Systems, February 2007.) In an implementation of the RBX technique, a RGB cross-polarized image of skin is transformed to a Red/Brown/X (RBX) color-space using a combination of a light transport model of skin and a spectral-dependent model of the source-detector configuration used in capturing the RGB image. The RBX color-space transformation is based upon random samplings of cross-polarized facial skin images obtained from a large population of patients with different skin types.

Due to restrictions on imaging geometry, image acquisition and processing, quality of image acquisition and illuminating optical components, polarizing filter misalignment, and/or calibration errors, it may not always be possible to capture a pure diffuse reflection image using cross-polarized imaging. The quality of the cross-polarized data tends to be compromised when using shallow angles for illumination or near-perpendicular angles for detection with respect to the imaging surface, such as when capturing multiple images from various angles for 3D imaging using stereo techniques. When the field-of-view is large, cross-polarization is compromised as one moves away from the central axis of the imaging plane. Cross-polarization is also compromised if the area being imaged is not flat but has appreciable curvature. The resultant data in either case is similar to that of a standard captured image which has both specular and diffuse reflection information. This limits the ability to obtain tissue pigmentation information using techniques such as the RBX and other techniques described above.

Good quality cross-polarized images can be obtained with closed imaging systems such as Canfield's VISIA imaging systems which provide a well controlled illumination and image capture environment. Cross-polarized images captured with such a system are of sufficient quality for obtaining good tissue pigmentation information using techniques such as the RBX and other techniques described above. Without such systems, however, it typically is not possible to obtain diffuse reflection images of sufficient quality from which good tissue pigmentation information can be extracted.

SUMMARY OF THE INVENTION

Embodiments of methods and apparatus in accordance with the present invention overcome the aforementioned shortcomings by providing the ability to estimate the diffuse reflection component of an image captured without cross-polarization, thereby making it possible, for example, to estimate skin pigmentation information from an image of skin captured conventionally. The image can be, for example, a total reflection image, obtained in a conventional manner by shining white light on the tissue and capturing the reflected light. There may also be cases in which the intent is to capture a diffuse reflection image, such as by using a cross-polarization imaging arrangement, but because of limitations such as those discussed above, a partially diffuse reflection image is captured. Embodiments in accordance with the present invention can also obtain the diffuse reflection components of such partially diffuse reflection images as well.

In an exemplary embodiment of a method in accordance with the present invention, a standard captured image of skin is analyzed to obtain an estimate of the surface reflection component. The surface reflection component can then be used to generate a surface reflection image which is useful for showing the distribution of light on the skin and/or to highlight superficial features such as wrinkles, fine lines, folds, pores, texture, and visible spots.

Exemplary methods in accordance with the present invention include a training procedure in which a set of transformation parameters are obtained for a given imaging system and a suitable classification of the subject skin (e.g. skin type). These transformation parameters can then be used for processing skin images captured by the imaging system to obtain the diffuse and/or surface reflection components of the images. The diffuse and/or surface reflection components can then be further processed to obtain pigmentation images and/or surface reflection images, respectively. The resultant images can then be further processed, for example, such as by automated segmentation/detection and evaluation techniques or the like.

The above and other aspects and features of the present invention will be apparent from the drawings and detailed description which follow.

DETAILED DESCRIPTION

Figure 1:
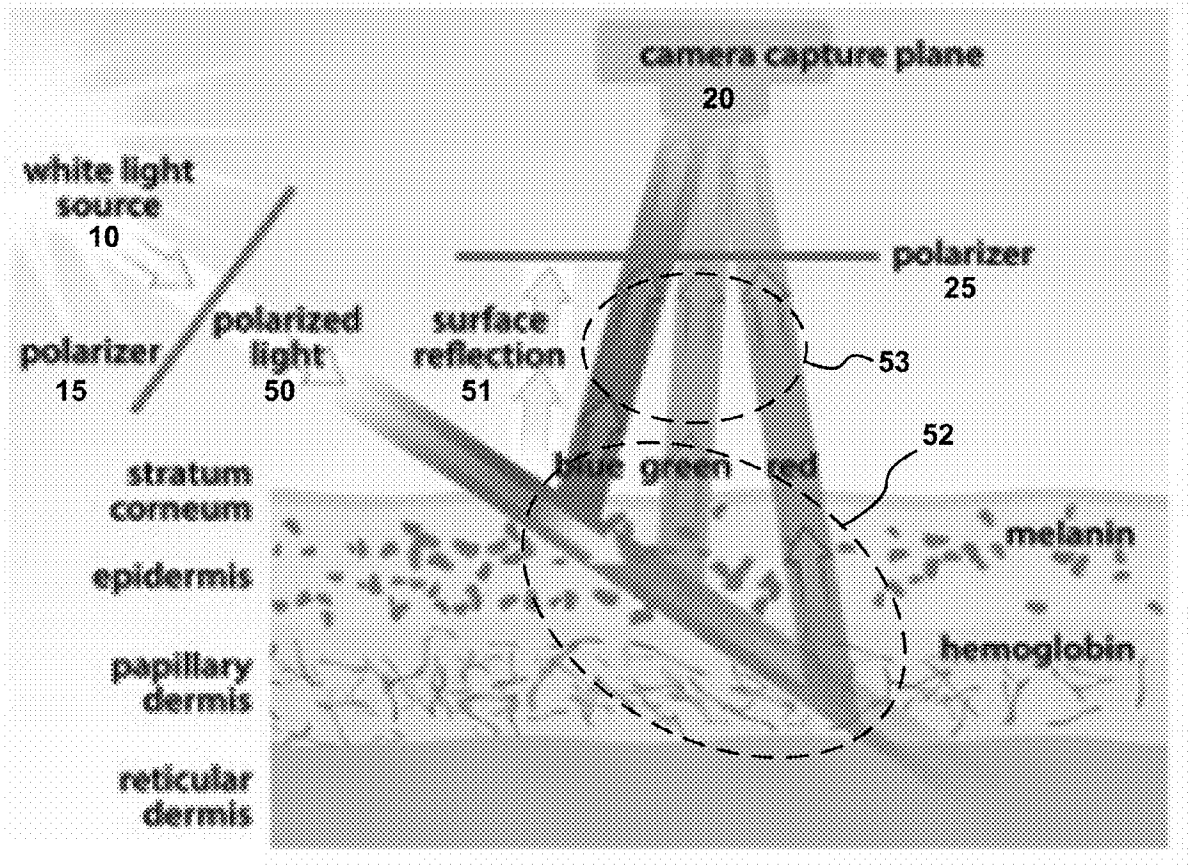
FIG. 1 (Prior Art)
FIG. 1 illustrates the remittance of light from the structures of normal skin and a conventional polarized image capture arrangement.
Figure 2:
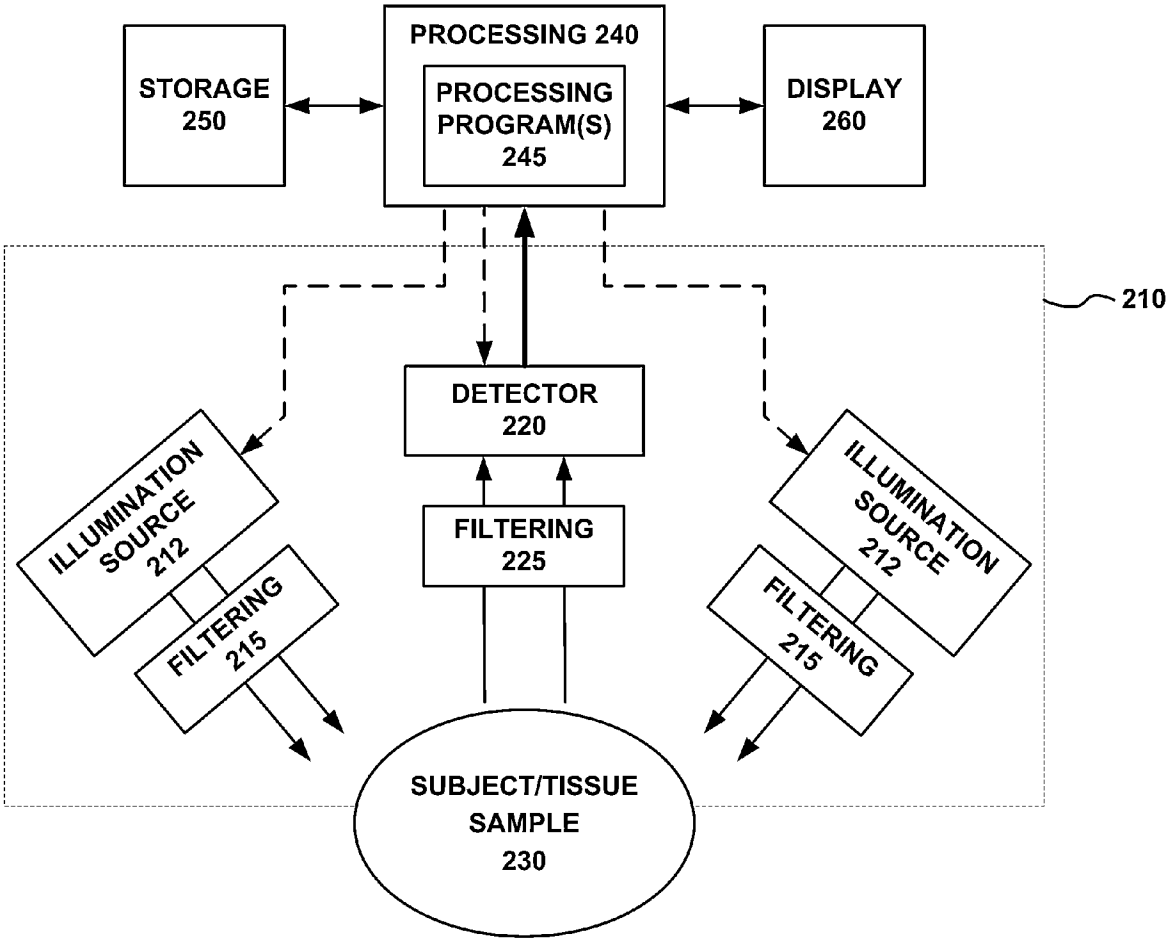
FIG. 2 is a schematic representation of an exemplary tissue imaging and processing system.

FIG. 2 schematically depicts an exemplary embodiment of a tissue imaging and processing system 200 in accordance with the present invention, for capturing and processing images of tissue to be studied, such as skin. The major components of system 200 include an imaging apparatus 210 coupled to a processing block 240. As described more fully below, imaging apparatus 210 may include a wide variety of systems and/or devices such as, for example, a digital camera, preferably with flash, or a closed environment imaging booth. Image data captured by imaging apparatus 210 is provided to processing block 240 for processing. Processing block 240 may also control imaging apparatus 210, such as by controlling the capture of images and/or illumination. Imaging apparatus 210 may also operate without being controlled by processing block 240, and only provide image data for processing.

As shown in FIG. 2, imaging apparatus 210 includes one or more illumination sources 212 which are activated to shine light onto a subject's skin or a tissue sample 230 through a respective filtering element 215. Light reflected from the subject tissue 230 is captured by a detector 220 through a filtering element 225. The filtering elements 215, 225 are optional and may include polarizers. For capturing cross-polarized images, the polarizers of the illumination source filtering elements 215 are preferably orthogonal to the polarizer of the detector filtering element 225. As discussed above, cross-polarization eliminates specular reflections from the skin surface, improving visibility of re-emitted light from the epidermis and dermis where melanin and hemoglobin, respectively, primarily reside. In addition to polarizers, the filtering elements 215, 225 may also introduce additional filtering and may include a plurality of filters, each of which can be selectively placed in the respective light path of the filtering element. (Note that the term "light" as used herein is not necessarily limited to humanly visible electromagnetic radiation, and may include portions of the electromagnetic spectrum above and below the visible range.)

Preferably, the detector 220 comprises a digital camera. The detector 220 may also comprise multiple one- or two-dimensional detectors, with similar or different characteristics. Multiple detectors 220 can be arranged to capture two- or three-dimensional images. The information and/or images captured by the detector 220 are provided to processing block 240 for image processing as described in greater detail below. The processing block 240 may be implemented, for example, with one or more computers, workstations, or the like, operating in accordance with one or more processing programs 245 stored in a suitable machine-readable medium. Processing block 240 may be coupled to storage 250, containing a database or the like, and a display 260.

Various types of illumination sources 212 may be used in the system 200. Preferably, xenon light is used as it provides a broad spectrum from which the various illumination spectral bands can be selected using the appropriate set of optical filters. However, LASER, tunable LASER, LED, LED arrays, halogen or other types of arc lamps, among others, may be used for the various modes of illumination contemplated by the present invention. Narrow-band illumination sources such as LEDs, for example, have the advantage of not requiring optical filtering to provide illumination for a specific spectral band. For applications requiring illumination in multiple spectral bands, however, multiple illumination sources would be required.

The illumination source(s) 212 may be pulsed or left continuously on, and may employ some form of shuttering mechanism, depending upon the type of detector 220 used.

One or more illumination sources 212 may be used in the exemplary system 200 to obtain the required illumination. Preferably, two illumination sources 212 are used to provide a more uniform illumination, but depending upon the size and shape of the tissue sample 230 or the area of the subject to be imaged, one or more than two sources can be used. Reflectors and/or optical diffusers may also be used to obtain the desired illumination characteristics.

The methods of the present invention are independent of the order in which images are captured. Where multiple images are captured, they are preferably captured in a sequence that will optimize the overall data acquisition time, switching restrictions imposed by the illumination sources, and any filter mechanism employed. If multiple detectors are used, then the capture sequence may also be dependent on the detector parameters.

In an exemplary embodiment, the detector 220 comprises a single camera due to ease in system control, low cost, and the ability to combine information from various images. Multiple cameras may be used, however, to capture different modes of images simultaneously; to capture images from various angles simultaneously; or to enable reconstruction of the three-dimensional shape of the tissue, or body part being imaged. In a further exemplary embodiment, one or more cameras that can be moved to image the subject tissue from different positions can also be used. As such, three-dimensional reconstructions can be accomplished with one camera.

Various types of cameras may be used in the present invention. Digital color cameras are preferred because they allow fast and automatic image capture, easy access to the images/data in an electronic format, and enable the capture of images under various modes of illumination. Other types of cameras such as monochrome cameras, standard 35 mm cameras, cameras that allow instant developing film, etc., may also be used. Further, while it is preferred to capture a digital image using a camera, an array of photo-detectors (e.g., photo diodes) with or without a scanning mechanism may be used.

In an exemplary embodiment, a series of images under different modes of illumination may be captured. In a further exemplary embodiment, the detector 220 may comprise one or more video cameras to capture a video recording under any of the modes of illumination. The video data may be displayed on a suitable monitor (including a display monitor built into the camera or display 260) in real-time. This is desirable for comparative evaluation and/or follow-up studies to ensure proper co-registration of the images. Furthermore, the video data may be processed and the processed information displayed either in real-time or later.

Acquisition of images in a digital format is preferred in order to facilitate storage and post-processing. Moreover, it is preferable to use a camera that provides a "raw" output (i.e., saves images in a raw data format). It is also preferred to use the raw data format images for post-processing and analysis as it would preserve the purity of the captured information. However, cameras that save images in other formats, such as jpeg/jpg, tiff/tif, etc may also be used for data collection. The post-processing may use the images stored in these various image formats. The images may be resized, color-and/or white-balance corrected, or converted from one format to another, including converting the "raw" images to some other format during the post-processing. Further, in an embodiment using an array of photo-detectors for image capture, the data may be post-processed before or after rendering the data as an image.

The captured image signal may also be provided directly to a display device such as, for example, an eye-piece, a goggle, a hand-held viewer, a monitor, or the like, thereby providing a live image. In an exemplary embodiment, the viewing device includes image detection, illumination, filtering, and magnification. Alternative embodiments may include any suitable combination of such features.

In embodiments of the present invention, it is preferred that light from the illuminating source(s) 212 fall directly (via filtering 215) onto the tissue being imaged. Also, it is preferred that the detector(s) 220 directly collect (via filtering 225) the light from the tissue being imaged. This kind of optical geometry provides a simple and compact configuration. However, use of indirect lighting and/or detection is possible, e.g., by using mirrors.

It is preferred to arrange the illumination sources 212 and the detector 220 in such a way that the angle formed by each source, the subject tissue, and the detector is in a range of approximately 45-50 degrees. For an angle smaller than 45-50 degrees, the penetration depth of the light into the tissue will be reduced. For an angle larger than 45-50 degrees, the amount of diffuse reflected light detected will be reduced. However, smaller or larger angles may be used for imaging due to space constraints, enhancing certain skin features, and/or enhancing the surface or diffuse reflectance signal.

It is contemplated that the present invention can be used with a wide variety of imaging apparatus 210, providing a wide variety of open or closed image capture environments. For example, the imaging apparatus 210 may include just a hand-held digital camera with built-in flash, among other possibilities. Other examples of open-environment imaging systems that can be used include the VECTRA imaging system and the REVEAL imaging system from Canfield Scientific, Inc. Examples of closed-environment imaging systems include the DERMSCOPE, VISIA and VISIA-CR imaging systems available from Canfield Scientific, Inc. However, because systems such as VISIA and VISIA-CR are capable of providing high quality cross-polarization images, it is expected that the benefits of the present invention will be more notable for images captured with other, particularly open-environment systems. Nonetheless, the present invention can be applied to lower quality or partially cross-polarized images to improve the quality of the diffuse reflection component data conveyed therein. In addition to providing good diffuse reflection component data without a high quality cross-polarization image, the present invention can provide good specular reflection component data without a high quality parallel-polarization image (or with a partially parallel-polarized image). This allows for simpler image capture apparatus, without polarizing filters, that is easier to set up and operate, among other benefits. Moreover, the present invention can provide both diffuse and specular reflection component data from one image, as opposed to requiring two images captured under different conditions, namely one with cross-polarization and another with parallel-polarization. This eliminates image registration issues and reduces image setup, capture and processing time, among other benefits.

Figure 3:
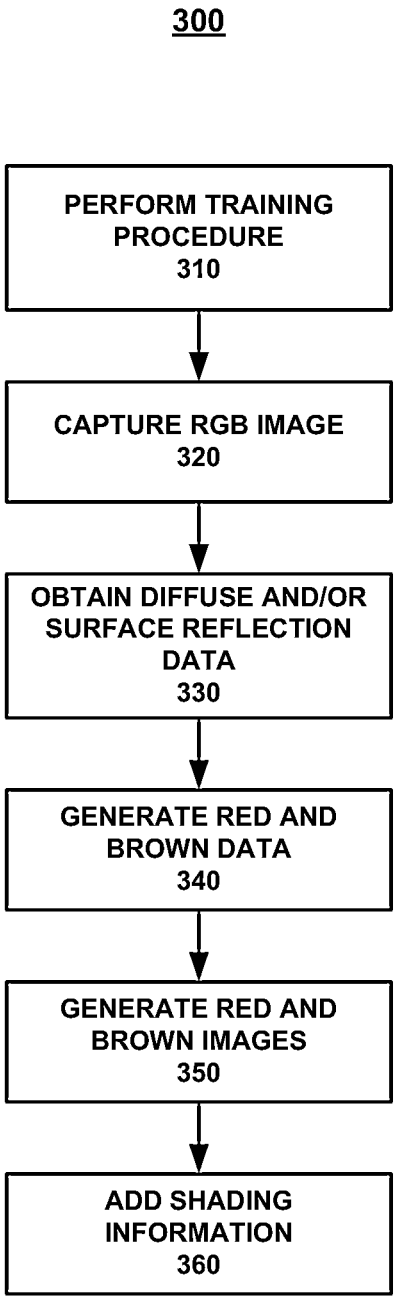
FIG. 3 is a flow chart depicting an exemplary method of capturing and analyzing skin images.

FIG. 3 is a high-level flow chart providing an overview of an exemplary embodiment of an image capture and analysis method 300 in accordance with the present invention. The method 300 can be carried out, for example, using system 200 of FIG. 2, with processing block 240 thereof operating in accordance with processing program(s) 245.

As shown in FIG. 3, the exemplary method 300 includes performing a training procedure 310 in which a set of transformation parameters are obtained for a given imaging system, such as imaging apparatus 210 of FIG. 2, and a suitable classification of the subject skin (e.g. skin type). For a given imaging system, a set of transformation parameters can be obtained for each of a plurality of skin types. The transformation parameters can then be used for processing a standard image of skin area captured by the imaging system to obtain the diffuse reflection and/or specular components of the image. An exemplary implementation of a training procedure is described in greater detail below.

It is contemplated that transformation parameters obtained for one imaging system can be used for other, similarly-configured imaging systems. For example, the transformation parameters obtained for a VECTRA system can be used for another VECTRA system configured with similar cameras, illumination sources and filtering.

Once the training procedure has been performed, the method proceeds to step 320 in which a RGB image is captured. As described above, a RGB image can be captured with the system 200 of FIG. 2 under a variety of illumination and capture conditions, ranging from standard, white-light total reflection image capture, to cross-polarized image capture. The image captured can be a total reflection image, a polarized (cross or parallel) image, or a partially (cross or parallel) polarized image.

At step 330, the captured image is processed using transformation parameters from training procedure 310 to estimate the diffuse reflection and/or surface reflection (specular) components of the image. It should be noted that if the captured image is a cross-polarized or partially cross-polarized image, it may not contain a surface reflection component strong enough to be recoverable, in which case only the diffuse reflection component is obtained. Moreover, if the captured image is a parallel-polarized image, it may not be possible to accurately estimate the diffuse reflection component, in which case only the surface reflection component is obtained.

As discussed above, it is contemplated that multiple sets of transformation parameters are obtained in the training procedure 310 for multiple skin types. In that case, in step 330, one of the multiple sets of transformation parameters is selected in accordance with the skin type of the subject and used to process the captured image of the subject.

At step 340, using transformation parameters obtained in the training procedure of step 310, a transformation is performed on the diffuse reflection component data obtained in step 330 to obtain pigmentation data. In an exemplary embodiment, an "RBX" color-space transformation is performed for this purpose. A description of this technique can be found in R. Demirli et al., "RBX Technology Overview," Canfield Imaging Systems, July 2007. As discussed, a Red component provides an indication of the distribution of hemoglobin in the imaged skin, whereas a Brown component provides an indication of the distribution of melanin, the primary chromophores found in skin.

Once the Red and Brown pigmentation data are generated at step 340, images thereof can be generated at step 350. The generated images can be displayed, stored or processed. In order to generate the images, the Red and Brown data derived from the captured RGB image are scaled and quantized in accordance with scaling and quantization threshold values determined in the training procedure 310. The Red and Brown data can be scaled and quantized, for example, into normalized eight-bit intensity values with a range of 0-255, which can be used to display gray scale images thereof, such as on display 260 of system 200 shown in FIG. 2. For a more realistic appearance when displayed, the intensity values or gray scale images can be translated into pseudo-color images, such as with a look-up table or other suitable translation arrangement. In an exemplary embodiment, a Red look-up table is used to convert the gray scale image representing the Red data into red colored images, and a Brown look-up table is used to convert the gray scale image representing the Brown data into brown colored images. For each gray scale value, each look-up table provides a RGB value for driving a display. The Red look-up table translates the Red gray scale values to a range of colors from white to bright red. Similarly, the Brown look-up table translates the Brown gray scale values to a range of colors from white to dark brown. It should be noted that although red and brown are preferred for representing hemoglobin and melanin, respectively, other colors can be used as well.

Although the Red and Brown data may be stored and processed without generating their respective images in step 350, representing the data in image form may be desirable as it allows for easier handling and processing. Furthermore, there are several known image compression techniques that can be applied to compress the images thereby reducing storage requirements. Moreover, even if there is no desire to display an image such as for example, an image of the diffuse reflection component which when displayed may not be particularly helpful to an observer it may nonetheless be useful to represent the diffuse component data in the form of an image for the aforementioned reasons.

When displayed, the resulting two-dimensional Red and Brown pseudo-color images may tend to appear flat and a bit grainer due to the reflection signal separation and de-noising involved in the transformation process. At step 360, more realistic images can be obtained by adding three-dimensional shading information to the results. The 3D shading added can be the one produced by the actual capture environment, in the case of three-dimensional imaging with multiple imaging detectors, or a simulated shading that is estimated based on the simulated positions of the illumination sources and detectors in the 3D space. If the original image capture system captures images using multiple cameras from different angles, the original, Red, Brown, and surface reflection images can be used in the three-dimensional reconstruction of the surface. Besides showing detailed information about the skin pigment distribution, the transformed images, and in particular the surface reflection image, also highlight topological features such as wrinkles, fine lines, folds, pores, texture, and visible spots. The pigmentation and topological features can be further processed such as being segmented for quantitative evaluation using known feature detection techniques.

Figure 4:
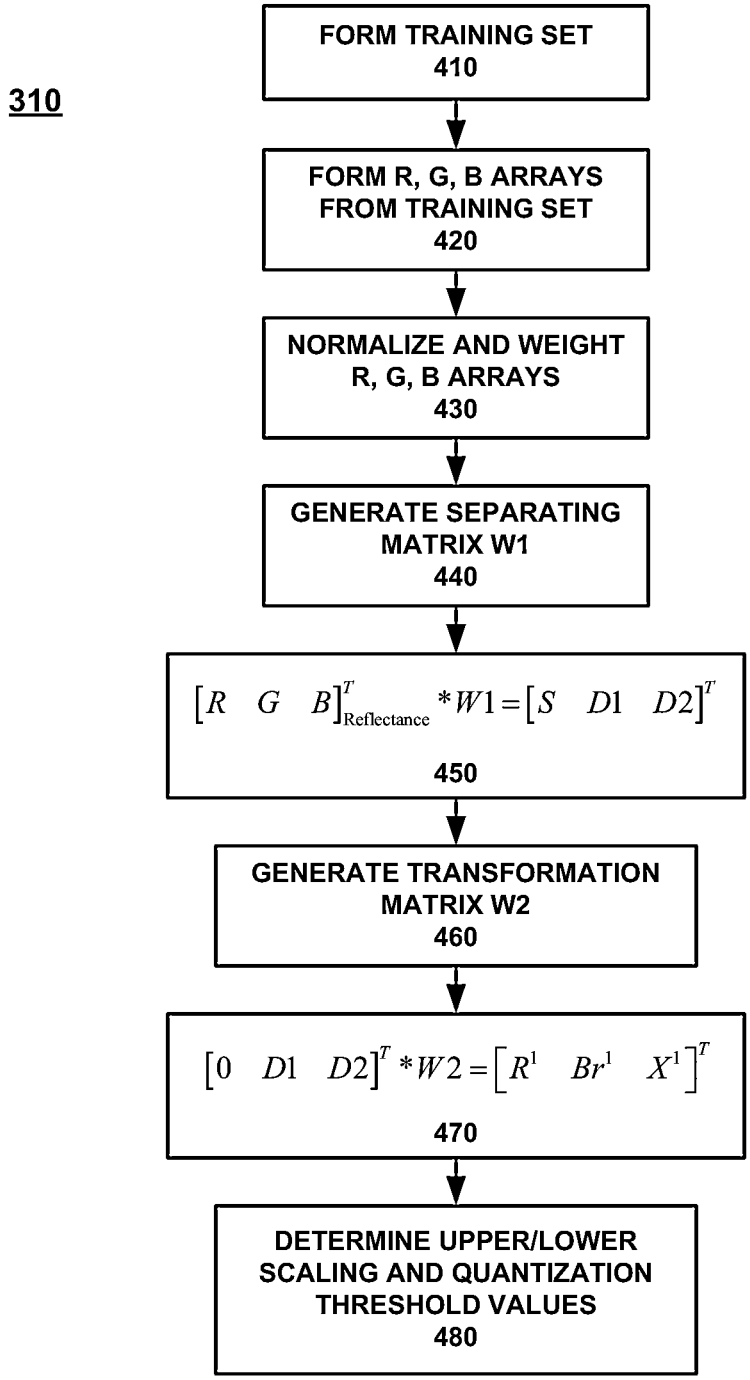
FIG. 4 is a flow chart depicting an exemplary training procedure for use in the method of FIG. 3.

An exemplary implementation of a training procedure 310 for use in the imaging method 300 described above will now be described with reference to FIG. 4 which shows a flowchart thereof.

For a given imaging configuration, a training set is formed at step 410 from multiple digital color images captured with that configuration. It is contemplated that an imaging configuration may include a combination of a variety of one or more light sources with or without polarizing/spectral filters, one or more cameras/detectors, other optical elements, positioning devices, and enclosures. In an exemplary embodiment, an imaging system 200 such as that described above with reference to FIG. 2 is used.

The training set may comprise skin images from a specific region-of-interest (ROI), such as the face or portions thereof, of subjects of a given race, skin type, age, and/or gender. The number of images and the types of subjects used in a training set can vary based on the objectives of the study. For example, if a study entails evaluating pigmentation changes in Caucasian skin, the training set can be formed using images of Caucasian subjects alone. Multiple training sets can be formed for multiple skin types. A database can be built and stored such as in storage 250 for use by processing block 240. In an exemplary embodiment, each training set includes approximately 30-80 images, with skin types classified in accordance with a known, standard scale such as the Fitzpatrick scale, or the like. A separate, East Asian skin type class representative of skin typically having greater concentrations of bilirubin than those on the Fitzpatrick scale can also be included. For a general purpose imaging system, a mixed population containing all skin types is included in the training.

The ROI in each image of the training set can be selected either manually or detected automatically such as by using any suitable automated segmentation/detection technique. At step 420, the respective red (R), green (G) and blue (B) values for all or a subset of pixels within the ROI, and for all or a subset of the images in the training set are mixed together and vectorized to obtain R, G and B measurement vectors, or arrays. Upon mixing, information indicative of the source of each R, G and B measurement value (i.e., from which image, and/or of which skin type) can be ignored. Moreover, the order in which the measurements are mixed can follow a particular pattern or be random (e.g., the values of the pixels of an image can be mixed together before mixing in those of another image, or the values of pixels from different images can be randomly mixed, among other possibilities.)

While images in any format and color-space can be used, it is preferable to use images in raw format so as to obtain the R, G and B values from a linear color-space. It is also preferred to use this raw data for post-processing and analysis as it would preserve the purity of the physiological information to be extracted. However, images in other formats (e.g., jpeg, tiff, bmp) may also be used for data collection and post processing. Further, in the case where an array of photodetectors is used for data collection, the data may be post-processed before and/or after rendering the data as an image.

At step 430 of the exemplary training procedure, the R, G, and B measurement arrays formed from the pixel values of the training set images, are normalized and weighted to account for one or more of a variety of factors, such as: the wavelength-dependent output and response of the illumination and detection elements of the imaging system with which the images were captured; the geometry of the illumination and detection configuration, such as the angles of incidence and detection, which influences the relative strength of surface and diffuse reflections; and/or the wavelength-dependent refractive indices of air and skin. For instance, each camera has a different color response. The color response of a camera can be measured by capturing a series of images of a standard color chart (e.g. a Macbeth color chart) having various color chips and chips with known shades of gray under various intensities of illumination. A three-dimensional RGB color response of the camera is then obtained by measuring values from the various color chips and comparing them to the expected standard color values for those chips. This 3D plot also indicates whether or not the color response of the camera is linear. Using such measurements characterizing the camera's response, correction and/or normalization of the RGB values from an image can then be performed.

In an exemplary embodiment, independent component analysis (ICA) is then performed at step 440 using the normalized and weighted R, G and B arrays to generate a 3×3 separating matrix W1 that models the non-mixing of the surface reflection signal and the diffuse reflection signal in the images of the training set. ICA techniques are described in A. Hyvärinen et al., "Independent Component Analysis: Algorithms and Applications," Neural Networks, 13(4-5): 411-430, 2000.

The separating matrix W1 is then used at step 450 to transform the normalized and weighted R, G and B arrays into a surface reflection component S and two additional independent components D1 and D2 in accordance with the following expression:

$$[R\ G\ B]_{Reflectance}^{T} * W1 = [S\ D1\ D2]^{T} \quad (1)$$

The independent components D1 and D2 include the diffuse reflection information. D1 and D2 can be used as a reduced set of training data (in which all the values in vector S are replaced with zeros) before being subjected to further processing, such as evaluating tissue pigmentation and/or scattering. Any of the techniques described above for evaluating diffuse reflection images for tissue pigmentation information can be used for processing this transformed training set. It should be noted that while a pigmentation evaluation technique such as the RBX technique can provide pigmentation data based on D1 and D2 as input data, other techniques may require a single diffuse reflection component. Such a component can be obtained as a linear combination of D1 and D2 (e.g., D=aD1+bD2.) Equivalently, a linear transformation of separating matrix W1 can be determined so that when applied to the RGB reflectance data a single diffuse reflection component D results.

Operation then proceeds to step 460 in which a color-space transformation matrix W2 is determined for transforming the diffuse reflection information into pigmentation data. In a preferred embodiment, the color-space transformation matrix W2 is obtained in a procedure that uses the RBX color-space transformation technique. As mentioned above, the RBX technique allows decomposition of cross-polarized digital color images into skin pigmentation data. The RBX technique uses a light transport model that assumes two dominant chromophores in the skin: melanin primarily residing in the epidermal layer, and hemoglobin primarily residing in the dermal layer along with the light scattering properties associated with various skin layers.

Further, the spectral profile of the optical components (light sources, filters and camera/detector) are measured along with the color response of the camera/detector. The color verses spectral response of the system components is evaluated against the skin light transport model using randomly sampled skin images as measurements to derive a transformation matrix for decomposing the cross-polarized color image of the skin captured by the camera into pigmentation maps. When processing an input image, the decomposition parameters work in a similar fashion as a color-space transformation converting the RGB image into Red, Brown and X (RBX) data. The Red and Brown data represent the hemoglobin and melanin pigment information, respectively.

The RBX technique defines the RGB to RBX color-space transformation for an imaging system that can capture a true cross-polarized image. This transformation can be expressed as follows:

$$[R\ G\ B]_{Cross\text{-}polarized}^{T} * W2 = [R^1\ Br^1\ X^1]^T. \quad (2)$$

W2 is a 3×3 transformation matrix, which in an exemplary embodiment is determined in a training procedure in which an imaging system is used to capture random samplings of cross-polarized skin images selected from a large population of subjects with different skin types. The imaging system used in this RBX training procedure preferably includes the same or similar optical components (camera, light sources, filters) as that of the imaging system used in method 300 to capture the RGB reflectance images of individual subjects. This RBX training system, however, is configured to capture high quality cross-polarized images.

Substituting the cross-polarized image RGB values in Eq. 2 with values in the reduced set of training data obtained using Eq. 1 (where S is substituted by a zero vector) yields the following expression:

$$[0\ D1\ D2]^T * W2 = [R^1\ Br^1\ X^1]^T \quad (3)$$

Using the transformation matrix W2 determined in the RBX training procedure allows conversion of the diffuse reflection information in components D1 and D2 into Red ($R^1$) and Brown ($Br^1$) components in accordance with Eq. 3. The Red ($R^1$) and Brown ($Br^1$) components are very similar to the Red and Brown components one would obtain with the RBX technique using a cross-polarized image.

Although other color-space transformations can be used for evaluating diffuse reflection images for tissue pigmentation information, the RBX color-space transformation is preferred because it is based on the spectral response of the specific imaging system and accounts for variations in skin types by means of the mixed training set used in obtaining the color-space transformation matrix W2.

The training procedure then continues to step 470 in which the reduced training set of diffuse reflection information D1 and D2 is transformed, in accordance with Eq. 3, into Red and Brown data using the color-space transformation matrix W2.

Then, at step 480, upper and lower scaling values and quantization threshold values are calculated for both the Red and Brown data using, for example, histogram-based percentile calculations. These values can be used to scale and quantize the Red and Brown data derived from an image of a subject. The scaled and quantized Red and Brown data can then be used to generate images, as described above.

It should be noted that steps 470 and 480 can be skipped if there is no need to determine scaling and quantization values based on the training data. This may be the case, for example, where there is no need to compare images of the pigmentation data. In that case, the scaling and quantization values for an image can be determined from the pigmentation data obtained for that image. For applications in which images are to be compared (e.g., of different subjects or sequential images of the same subject), scaling and quantization values based on the training data provide a common reference thereby allowing for more accurate comparisons of different images.

As such, the exemplary training procedure 310 produces—for a given imaging system and suitable classification of subject skin (e.g. skin type)—a separating matrix W1, a color-space transformation matrix W2, and a set of scaling and quantization threshold values for the Red and Brown information. This data can then be used for processing a standard image of skin area captured by the imaging system to obtain the Red and Brown images thereof. With reference to the method 300 of FIG. 3, the separating matrix W1 generated by the training procedure 310 is used in step 330 to process a captured RGB image in accordance with Eq. 1 to obtain the diffuse reflection components of the image; the color-space transformation matrix W2 is used in step 340 to perform a color-space transformation on the diffuse reflection components to obtain the Red and Brown component data; and the scaling and quantization threshold values are used in step 350 to generate images from the Red and Brown data. The resultant Red and Brown images can be used as hemoglobin and melanin absorption maps, respectively, providing a visual display of the distribution of hemoglobin and melanin in the subject tissue imaged.

In an exemplary embodiment, the separating matrix W1 can be used in step 330 to process a captured RGB image in accordance with Eq. 1 to obtain the surface reflection component S. To generate an image of the surface reflection component S, upper and lower scaling values and quantization threshold values can be obtained during the training procedure 310 using the surface reflection component S in similar manner as used to determine the Red and Brown upper and lower scaling and quantization threshold values. The surface reflection image is useful for showing the distribution of light (from the one or more illumination sources) on the imaged skin area, and highlighting superficial features such as wrinkles, fine lines, folds, pores, texture, and visible spots. By thus removing the diffuse component from the reflectance image thereby isolating the surface reflection component S, the resultant surface reflection image shows surface features with greater clarity and contrast, making them easier to detect, both visually and by further automated analysis of the image. In an exemplary embodiment, the gray scale surface reflection image can be transformed into a color image using a color look-up table. This helps highlight features, such as skin texture, pores, wrinkles, shine, or hot-spots due to the lighting environment. Thus for instance, lighting hot-spots on the imaged skin area can be represented with colors ranging from red for moderately hot-spots to yellow for hotter spots.

Additionally, in an exemplary embodiment, steps 330 and 340 can be combined so that a reflectance RGB image captured in step 320 can be transformed directly into Red ($R^1$) and Brown ($Br^1$) components in accordance with the following expression:

$$[R\ G\ B]_{Reflectance}^{T} * W3 = [R^1\ Br^1\ X^1]^T. \quad (4)$$

Transformation matrix W3 can be derived from W1 and W2. In an exemplary embodiment:

$$W3 = W1 * [W2_1\ W2_2\ 0], \quad (4a)$$

$W2_1$ and $W2_2$ are the first and second columns of the RBX transformation matrix W2, as determined above, with its third column set to zero. Such an embodiment may be desirable, for example, in applications where processing speed and/or storage resources are limited or there is no need to obtain the surface reflection component S.

Illustrative applications of the processed Red, Brown and surface reflection images include: identifying scars and spots; evaluating pigmentary changes; evaluating skin damage/aging; classifying inflammatory from non-inflammatory lesions; evaluating erythema by analyzing the hemoglobin information; detecting wrinkles or predicting future wrinkle development; evaluating skin hydration levels; evaluating and/or classifying normal, dysplastic, and malignant lesions; evaluating various skin pathologies such as roseacea, hyperpigmentation, skin burn, irritation, and inflammation; classifying acne lesions (e.g., open comedone, closed comedone, papule, pustule, nodule, burnt-out lesion, excruciated lesion); evaluating or recommending treatment products and procedures; generating, displaying and analyzing simulated images that estimate/predict the past/future characteristics of skin.

The techniques described herein can be used advantageously in conjunction with systems such as Canfield Scientific Inc.'s 3D imaging system, VECTRA, which uses multiple cameras and multiple sources located at different positions in the three dimensional space with respect to the imaging surface. The VECTRA system is used for reconstructing 3D surfaces from 2D images using stereo processing techniques. Capturing equal quality, cross-polarized images with multiple cameras, however, puts unacceptable restrictions on the positions and orientations of the light sources and the cameras. Further, the quality of the captured cross-polarized images will depend on the sequence in which the sources are fired. If all the sources are fired together, it will be extremely difficult to get the correct orientations of the polarizing filters for capturing cross-polarized or parallel-polarized images. Capturing standard images, on the other hand, is much simpler and the techniques described herein, which automatically account for and separate the light distribution/gradient component, will be highly beneficial in this regard. Besides providing the ability to noninvasively evaluate skin pigment distribution, knowledge of the light distribution/gradient will allow image normalization, which is extremely important for image analysis. Normalization will reduce the spatial variance in the image contrast for better feature detection or segmentation.

Another application of the techniques presented herein is in conjunction with a hand-held imaging device that records a streaming video signal for real-time processing, display and analysis. With a hand-held imaging device, it is difficult to maintain the quality of cross-polarized video data due to the movement of the imaging device or the subject, as the device scans the skin surface being imaged. Both standard and cross-polarized image or video data capture would be required for treatment procedures that depend on sub-surface pigment information, surface features, and color information. Switching between standard and polarized imaging modes while capturing and processing the streaming video signal would put unacceptable restrictions on the captured and displayed frame rate. The techniques presented herein remove the requirement of capturing both standard and polarized images while still providing all the required information. This should also make the data processing and display at least two times faster.

The diffuse and surface reflection data can also be used in evaluating the scattering properties of tissue for various other applications.

While embodiments of the present invention have been described above for captured RGB images, embodiments of the present invention can also be implemented for applications in which the captured images are monochrome. Such images can be captured, for example, with a multi-spectral imaging system that captures a series of monochrome images by illuminating the surface using a series of specific wavelengths. The illumination wavelengths may be monochromatic red, green and blue or may consist of or further include other wavelengths.

In an exemplary embodiment, the training sets of images may comprise monochromatic red, green and blue images from which the R, G, and B measurement arrays are formed. The above-described transformation parameters can then be determined for each color and applied to monochromatic captured images for determination of diffuse and/or surface reflection components and/or red and brown color components.

While embodiments of the present invention have been described above in which the input data is in a three-dimensional color (or channel) space (namely, red, green and blue), embodiments of the present invention can also be implemented for applications in which the input data is N-dimensional where $N \geq 2$, as in the case of multi-spectral measurements. Such embodiments may allow for skin constituents other than hemoglobin and melanin, such as bilirubin among others to be evaluated and imaged. Using a pigmentation evaluation technique analogous to RBX, for example, a Yellow pigmentation data can be estimated from a diffuse reflection image. The Yellow pigmentation data can be processed similarly to the Red and Brown data, as described above, and an image thereof generated and displayed to provide an indication of bilirubin distribution. In general, the dimensionality of the input data should be one greater than the number of independent components to be determined. As such, for example, to determine Red, Brown and Yellow pigmentation information, four input channels (e.g., R, G, B, and UV or R, G, B1 and B2) should be used for the input data.

The foregoing merely illustrates the principles of the invention and it will thus be appreciated that those skilled in the art will be able to devise numerous alternative arrangements which, although not explicitly described herein, embody the principles of the invention and are within its spirit and scope. For example, although illustrated in the context of separate functional elements, these functional elements may be embodied on one or more integrated circuits (ICs), discrete circuitry or combinations thereof, and/or in one or more stored program-controlled processors (e.g., a microprocessor or digital signal processor (DSP)), among other possibilities. It is therefore to be understood that numerous modifications may be made to the illustrative embodiments and that other arrangements may be devised without departing from the spirit and scope of the present invention as defined by the appended claims.

What is claimed:

1. A computer implemented method of processing a reflection image of tissue comprising:

performing a training procedure, including determining a first transformation;

estimating [at least one of] a diffuse reflection component [and a surface reflection component] of the reflection image, including applying the first transformation to the reflection image;

[generating an image of at least one of the diffuse reflection component and the surface reflection component of the reflection image]

*estimating data of at least one pigmentation from the diffuse reflection component of the reflection image;*

*generating a pigmentation image from the data of the at least one pigmentation*; and performing a further operation on the *pigmentation* image including at least one of storing, processing [and] *or* displaying the *pigmentation* image, wherein performing the training procedure includes determining parameters for [generating the image of the at least one of] *estimating* the diffuse reflection component [and the surface reflection component].

2. The method of claim 1, wherein the first transformation is determined in accordance with an independent component analysis (ICA).

3. The method of claim 1, wherein:

performing a training procedure includes determining a second transformation, and the step of estimating includes applying the second transformation to the diffuse reflection component.

4. The method of claim 3, wherein performing the training procedure includes determining parameters for generating [a] *the* pigmentation image.

5. The method of claim 1, wherein the reflection image is a total reflection image, a polarized image, or a partially polarized image.

6. The method of claim 1, wherein the reflection image includes a Red/Green/Blue (RGB) image.

[7. The method of claim 1, wherein the reflection image is an N-dimensional channel space image, where N≥2.]

8. A computer implemented method of processing a reflection image of tissue comprising:

performing a training procedure, including determining a first transformation;

estimating [at least one of] a diffuse reflection component [and a surface reflection component] of the reflection image, including applying the first transformation to the reflection image;

[generating an image of at least one of the diffuse reflection component and the surface reflection component of the reflection image]

*estimating data of at least one pigmentation from the diffuse reflection component of the reflection image;*

*generating a pigmentation image from the data of the at least one pigmentation*; and performing a further operation on the *pigmentation* image including at least one of storing, processing [and] *or* displaying the *pigmentation* image, wherein performing the training procedure includes:

forming at least one measurement array from pixels of a plurality of training images; and processing the at least one measurement array to account for at least one characteristic of an imaging apparatus used to capture the plurality of training images, wherein the at least one characteristic includes at least one of a wavelength-dependent output of an illumination source of the imaging apparatus, a wavelength-dependent response of a detector of the imaging apparatus, an illumination and detection configuration of the imaging apparatus, [and] *or* a wavelength-dependent refractive index of air and skin.

9. The method of claim 1, wherein the first transformation is a function of at least one of a skin type [and] *or* an imaging apparatus used to capture the reflection image.

10. A computer implemented method of processing a reflection image of tissue comprising:

performing a training procedure, including determining a first transformation;

estimating [at least one of] a diffuse reflection component [and a surface reflection component] of the reflection image, including applying the first transformation to the reflection image;

[generating an image of at least one of the diffuse reflection component and the surface reflection component of the reflection image]

*estimating data of at least one pigmentation from the diffuse reflection component of the reflection image;*

*generating a pigmentation image from the data of the at least one pigmentation*; and performing a further operation on the *pigmentation* image including at least one of storing, processing [and] *or* displaying the *pigmentation* image, wherein the first transformation is a function of at least one of a skin type [and] *or* an imaging apparatus used to capture the reflection image.

11. The method of claim 1, wherein the parameters include at least one of scaling, quantization, [and] *or* color translation parameters.

[12. The method of claim 3, wherein the parameters include at least one of scaling, quantization, and color translation parameters.]

[13. The method of claim 12, wherein the color translation parameters include parameters for translating the pigmentation image into at least one of a Red, Brown, and Yellow image.]

14. The method of claim 1 comprising:

estimating [data of at least one pigmentation from the diffuse reflection component of the reflection image] *a surface reflection component of the reflection image, including applying the first transformation to the reflection image, wherein performing the training procedure includes determining parameters for estimating the surface reflection component*; and generating [a pigmentation image from the data of the at least one pigmentation] *an image of at least one of the diffuse reflection component or the surface reflection component of the reflection image*.

15. The method of claim [14] *1*, wherein the data of the at least one pigmentation is indicative of at least one of hemoglobin, melanin, [and] *or* bilirubin.

16. The method of claim [14] *1*, wherein estimating data of the at least one pigmentation includes performing at least one of a color-space transformation, a principle component analysis (PCA), an independent component analysis (ICA), [and] *or* a Red/Brown/X transformation.

17. The method of claim [14] *1* comprising:

performing a further operation on the pigmentation image including at least one of storing, processing [and] *or* displaying the pigmentation image.

18. The method of claim [17] *1* comprising:

adding shading information to the pigmentation image.

19. The method of claim 1, wherein the reflection image includes *an N-dimensional color channel image or* N images, each image representing a [color-space] *color* channel, where N≥2.

*20. The method of claim 1, wherein generating the pigmentation image includes translating the data of the at least one pigmentation into at least one of a Red, Brown, or Yellow pseudo-colored image.*

*21. A computer implemented method of processing a reflection image of tissue comprising:*

*estimating data of at least one pigmentation from the reflection image, including applying a transformation determined in a training procedure to the reflection image;*

*generating a pigmentation image from the data of the at least one pigmentation; and*

*performing a further operation on the pigmentation image including at least one of storing, processing or displaying the pigmentation image.*

*22. The method of claim 21, wherein the reflection image is a total reflection image, a polarized image, or a partially polarized image.*

*23. The method of claim 21, wherein the reflection image includes a Red/Green/Blue (RGB) image.*

*24. The method of claim 21, wherein the reflection image includes an N-dimensional color channel image or N images, each image representing a color channel, where N≥2.*

*25. The method of claim 21, wherein the data of the at least one pigmentation is indicative of at least one of hemoglobin, melanin, and bilirubin.*

*26. The method of claim 21, wherein the transformation is determined in accordance with at least one of a color-space transformation, a principle component analysis (PCA), an independent component analysis (ICA), or a Red/Brown/X transformation.*

*27. The method of claim 21 comprising:*

*adding shading information to the pigmentation image.*

*28. The method of claim 21, wherein parameters for generating the pigmentation image include at least one of scaling, quantization, or color translation parameters.*

*29. The method of claim 28, wherein the color translation parameters include parameters for translating the data of the at least one pigmentation into at least one of a Red, Brown, or Yellow pseudo-colored image.*

*30. The method of claim 21, wherein the training procedure includes:*

*forming at least one measurement array from pixels of a plurality of training images; and*

*processing the at least one measurement array to account for at least one characteristic of an imaging apparatus used to capture the plurality of training images, wherein the at least one characteristic includes at least one of a wavelength-dependent output of an illumination source of the imaging apparatus, a wavelength-dependent response of a detector of the imaging apparatus, an illumination and detection configuration of the imaging apparatus, or a wavelength-dependent refractive index of air and skin.*

*31. The method of claim 21, wherein the transformation is a function of at least one of a skin type or an imaging apparatus used to capture the reflection image.*

*32. The method of claim 21 comprising:*

*estimating at least one of a diffuse reflection component or a surface reflection component of the reflection image, including applying another transformation to the reflection image;*

*generating an image of at least one of the diffuse reflection component or the surface reflection component of the reflection image; and*

*performing a further operation on the image of the at least one of the diffuse reflection component or the surface reflection component of the reflection image, including at least one of storing, processing or displaying the image of the at least one of the diffuse reflection component or the surface reflection component of the reflection image.*

*33. Apparatus for processing a reflection image of tissue comprising:*

*a storage device for storing instructions; and*

*a processor configured to process the instructions to:*

*estimate data of at least one pigmentation from the reflection image, including applying a transformation determined in a training procedure to the reflection image;*

*generate a pigmentation image from the data of the at least one pigmentation; and*

*perform a further operation on the pigmentation image including at least one of storing, processing or displaying the pigmentation image.*

*34. The apparatus of claim 33, wherein the reflection image is a total reflection image, a polarized image, or a partially polarized image.*

*35. The apparatus of claim 33, wherein the reflection image includes a Red/Green/Blue (RGB) image.*

*36. The apparatus of claim 33, wherein the reflection image includes an N-dimensional color channel image or N images, each image representing a color channel, where N≥2.*

*37. The apparatus of claim 33, wherein the data of the at least one pigmentation is indicative of at least one of hemoglobin, melanin, or bilirubin.*

*38. The apparatus of claim 33, wherein the transformation is determined in accordance with at least one of a color-space transformation, a principle component analysis (PCA), an independent component analysis (ICA), or a Red/Brown/X transformation.*

*39. The apparatus of claim 33, wherein parameters for generating the pigmentation image include at least one of scaling, quantization, or color translation parameters.*

*40. The apparatus of claim 39, wherein the color translation parameters include parameters for translating the data of the at least one pigmentation into at least one of a Red, Brown, or Yellow pseudo-colored image.*

*41. The apparatus of claim 33, wherein the transformation is a function of at least one of a skin type or an imaging apparatus used to capture the reflection image.*

*42. The apparatus of claim 33 wherein the processor is configured to process instructions to:*

*estimate at least one of a diffuse reflection component and a surface reflection component of the reflection image, including applying another transformation to the reflection image;*

*generate an image of at least one of the diffuse reflection component and the surface reflection component of the reflection image; and*

*perform a further operation on the image including at least one of storing, processing or displaying the image.*

*43. The apparatus of claim 33 comprising an image capture device, wherein the reflection image of tissue is captured by the image capture device.*

*44. A non-transitory computer-readable storage medium having stored thereon a computer program for processing a reflection image of tissue, the computer program comprising instructions for causing a computer to:*

*estimate data of at least one pigmentation from the reflection image, including applying a transformation determined in a training procedure to the reflection image;*

*generate a pigmentation image from the data of the at least one pigmentation; and*

*perform a further operation on the pigmentation image including at least one of storing, processing or displaying the pigmentation image.*

*45. The storage medium of claim 44, wherein the transformation is a function of at least one of a skin type or an imaging apparatus used to capture the reflection image.*

* * * * *